(12) United States Patent
Campbell, Jr.

(10) Patent No.: US 9,814,240 B2
(45) Date of Patent: Nov. 14, 2017

(54) STRENGTHENED GLASS WITH BIOCIDAL PROPERTY

(71) Applicant: Microban Products Company, Huntersville, NC (US)

(72) Inventor: Alvin Lamar Campbell, Jr., Huntersville, NC (US)

(73) Assignee: Microban Products Company, Huntersville, NC (US)

( * ) Notice: Subject to any disclaimer, the term of this patent is extended or adjusted under 35 U.S.C. 154(b) by 0 days.

(21) Appl. No.: 14/948,544

(22) Filed: Nov. 23, 2015

(65) Prior Publication Data

US 2016/0143291 A1   May 26, 2016

Related U.S. Application Data

(60) Provisional application No. 62/084,229, filed on Nov. 25, 2014, provisional application No. 62/187,611, filed on Jul. 1, 2015.

(51) Int. Cl.
*A01N 59/00* (2006.01)
*A01N 59/16* (2006.01)

(52) U.S. Cl.
CPC .................... *A01N 59/16* (2013.01)

(58) Field of Classification Search
CPC ................ A61K 33/38; A01N 59/16
USPC ................. 424/600, 618
See application file for complete search history.

(56) References Cited

U.S. PATENT DOCUMENTS

| | | | | |
|---|---|---|---|---|
| 6,143,318 A | * | 11/2000 | Gilchrist | A61K 33/22 424/404 |
| 6,831,028 B1 | * | 12/2004 | Ishii | A01N 59/16 428/401 |
| 7,704,903 B2 | * | 4/2010 | Seneschal | A01N 59/26 501/10 |
| 2005/0069592 A1 | | 3/2005 | Fechner et al. | |
| 2005/0233888 A1 | * | 10/2005 | Seneschal | A01N 59/26 501/45 |
| 2006/0142413 A1 | | 6/2006 | Zimmer et al. | |
| 2007/0122356 A1 | * | 5/2007 | Kessler | A61K 6/0017 424/49 |
| 2008/0044488 A1 | * | 2/2008 | Zimmer | B82Y 30/00 424/600 |
| 2014/0193499 A1 | | 7/2014 | Da Fonte Ferreira et al. | |

OTHER PUBLICATIONS

International Search Report and Written Opinion of corresponding application PCT/US2015/062407, dated Feb. 5, 2016, all enclosed pages cited.

* cited by examiner

*Primary Examiner* — Noah Wiese
(74) *Attorney, Agent, or Firm* — Nelson Mullins Riley & Scarborough LLP

(57) ABSTRACT

A biocidal additive formulation comprises a silver containing glass particle, and a combination of at least two metal based compounds. A metal in each of the metal based compounds is selected from the group consisting of silver, copper, zinc, mercury, tin, lead, bismuth, barium, cadmium, chromium, titanium, and a combination thereof. Another biocidal additive formulation comprises a silver containing glass particle, ZnO, and $Bi_2O_3$. A glass substrate possessing a durable biocidal property and an article possessing a durable biocidal property are also provided.

10 Claims, No Drawings

STRENGTHENED GLASS WITH BIOCIDAL PROPERTY

CROSS-REFERENCE TO RELATED APPLICATIONS

This application claims priority from U.S. provisional patent application Ser. No. 62/084,229, filed on Nov. 25, 2014, and from U.S. provisional patent application Ser. No. 62/187,611, filed on Jul. 1, 2015, in the United States Patent and Trademark Office. The disclosures of which are incorporated herein by reference in their entireties.

FIELD OF THE INVENTION

The present invention relates to a strengthened glass and, more particularly, to a laminate glass possessing a durable biocidal property.

BACKGROUND OF THE INVENTION

The prevalence of glass products and components gives rise to many surfaces that can harbor bacteria, fungi and viruses. Common surfaces include, without limitation, the glass cover used on devices (e.g. automatic teller machines), touch screens (as found on, e.g., computers, tablets, cell phones, electronic book readers, automotive navigation and "infotainment" devices), and the like.

Many microbes are capable of surviving for minutes to hours after being deposited on a non-host surface. Such germs may be transferred from the contaminated surfaced to a person, as well as from person to person.

Recent work has shown that silver nano-particles are useful to impart antibacterial/antiviral properties to treated substrates. However, nanoscale metal particles are considered to have negative toxicological implications on humans and other living organisms and ecosystems in general. Further, nanoscale particulate contamination can impair beneficial processes utilizing biological agents, such as remediation of sewage and other waste materials.

There exists a need for a strengthened glass possessing durable biocidal properties and presenting a reduced toxicological risk.

SUMMARY OF THE INVENTION

The present invention relates to a biocidal additive formulation comprising a silver containing glass particle and a combination of at least two metal based compounds. A metal in each of the metal based compounds is selected from the group consisting of silver, copper, zinc, mercury, tin, lead, bismuth, barium, cadmium, chromium, titanium, and a combination thereof.

Another biocidal additive formulation in accordance with the invention comprises a silver containing glass particle, ZnO, and $Bi_2O_3$.

A glass substrate possessing a durable biocidal property and an article possessing a durable biocidal property are also provided.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

DETAILED DESCRIPTION OF THE INVENTION

The following description of the embodiments of the present invention is merely exemplary in nature and is in no way intended to limit the invention, its application, or uses. The present invention has broad potential application and utility, which is contemplated to be adaptable across a wide range of industries. The following description is provided herein solely by way of example for purposes of providing an enabling disclosure of the invention, but does not limit the scope or substance of the invention.

As used herein, the terms "microbe" or "microbial" should be interpreted to refer to any of the microscopic organisms studied by microbiologists or found in the use environment of a ceramic article or ceramic-glazed article. Such organisms include, but are not limited to, bacteria and fungi as well as other single-celled organisms such as mold, mildew and algae. Viral particles and other infectious agents are also included in the term microbe.

As well, "biocidal" and like terms should be interpreted as encompassing both microbe-killing as well as microbistatic activities. That is, it herein is considered efficacious if the biocidal substrate reduces the number of microbes on it, or if the composition retards the normal rate of microbial growth.

For ease of discussion, this description uses the terms microbial and biocidal to denote a broad spectrum activity (e.g. against bacteria and fungi). When speaking of efficacy against a particular microorganism or taxonomic rank, the more focused term will be used (e.g. antifungal to denote specific efficacy against fungal growth in particular).

Using the above example, it should be understood that efficacy against fungi does not in any way preclude the possibility that the same biocidal composition demonstrates efficacy against another class.

For example, discussion of strong antibacterial efficacy demonstrated by a disclosed embodiment should not be read to exclude the embodiment from also demonstrating antifungal activity, or vice versa. This method of presentation is adopted for ease of understanding and should not be interpreted as in any way limiting the scope of the disclosure.

The following brief discussion of tempered glass and in particular to laminate glass is provided as an aid to the reader. This discussion is presented in the context of the production of CORELLE® dishware. This dishware is described as a tempered glass product consisting of two different types of glass. The glass types are laminated into three layers: a core layer and two skin layers. The thermal bonding of these layers gives this dishware strength, durability, and chemical resistance. The dishware also is dishwasher-safe and microwave-safe.

Those skilled in the art recognize that the production process of tempered glass products may vary from that which is presented below, and that the glass manufacturing process disclosed herein is adaptable to other products.

A first embodiment is a biocidal additive formulation adapted for use in a glass substrate. The biocidal additive formulation comprises a combination of biocidal agents, as described more fully below.

A second embodiment disclosed herein is a method for making a biocidal glass.

A third embodiment is a tempered glass substrate possessing a durable biocidal property.

A fourth embodiment is an article constructed, in whole or in part, of tempered glass substrate possessing a durable biocidal property.

Turning now to the first embodiment, disclosed herein is a biocidal additive formulation suitable for use in the manufacture of strengthened glass including, but not limited to, tempered glass and laminate glass. The biocidal additive formulation comprises at least one metal-based compound. More preferably, the biocidal additive formulation comprises a plurality of metal-based compounds.

As an example, an additive formulation comprises a plurality of metal-based compounds such as two or more metal-based compounds. In this exemplary formulation, it is preferable that the two metals be different from one another. Alternatively, however, the two compounds can be based on the same metal but differ from one another in other aspects of the compound.

Examples of metals in the metal-based compounds include, but are not limited to, silver, copper, zinc, mercury, tin, lead, bismuth, barium, cadmium, chromium, titanium, and a combination thereof.

Metal-based compounds include, but are not limited to, metal oxides. Preferred metal oxides include, but are not limited to, oxides of silver, copper, zinc, bismuth, titanium, tin, and combinations thereof.

Another component in the biocidal additive formulation is a silver containing glass particle. A silver containing glass particle is intended to encompass any silver-containing compound that is primarily inorganic in nature (some organic component is permitted, although the primary portion is inorganic). For example, silver may be placed on the surface of glass particle through ion exchange and the silver is released at a certain rate.

Examples of materials that can be used for the silver containing glass particle include, but are not limited to, a silver salt or a silver-based ion-exchange compound. Silver salts may include, without limitation, acetate, benzoate, carbonate, iodate, iodide, lactate, laurate, nitrate, oxide, palmitate, and sulfadiazine compounds.

In general, silver-containing particles suitable for use include, but are not limited to, those of zeolites, glasses, hydroxyapatite, zirconium phosphate (e.g. ALPHASAN®, Milliken & Company, Spartanburg, S.C.) or other ion-exchanging ceramic particles, or any combination thereof. Examples of silver-containing glass particles include IB14 (Microban Products Company), Ionpure WPA, Ionpure ZAF, and Ionpure IPL (Ishizuka Glass, JP) as well as B5000 and B7000 (Ciba Specialty Chemicals).

In an aspect of the present invention, the silver containing glass particle is present in the biocidal additive formulation of the present invention in an amount of 0.5% to 2.5% by weight, wherein the weight percentage is based on a dry weight basis of the biocidal additive formulation.

The type and quantity of the biocidal agent in the biocidal additive formulation may vary depending upon the type and desired physical properties of the article it is found within. The primary guideline for determining the necessary quantity of biocidal additive is that enough should be present in the composition to provide a commercially acceptable degree of efficacy against the microbe(s) of concern. In most instances, the efficacy threshold is at least about a 1.5-log reduction in colony-forming bacterial units. More preferably, a 2-log reduction is attained.

In an aspect of the present invention, the biocidal additive formulation comprises a silver containing glass particle and a combination of at least two metal based compounds, wherein the metal of each of the metal based compounds is selected from the group consisting of zinc, bismuth, and a combination thereof. Preferably, the biocidal additive formulation comprises ZnO, $Bi_2O_3$, and a combination thereof.

In another aspect of the invention, the biocidal additive formulation comprises 5% to 85% zinc oxide, preferably in a range of 20% to 70%, wherein the weight percent is based on a dry weight basis of the biocidal additive formulation.

In another aspect of the invention, the biocidal additive formulation comprises 5% to 85% bismuth oxide, preferably in a range of 20% to 70%, wherein the weight percent is based on a dry weight basis of the biocidal additive formulation.

An example of a biocidal additive formulation in accordance with an aspect of the present invention comprises: 0.5% to 2.5% of a silver containing glass particle; 5% to 85% of ZnO, preferably 10% to 35% of ZnO; and 5% to 85% of $Bi_2O_3$, preferably 25% to 85% of $Bi_2O_3$, wherein percentages are by weight and are based on the dry weight of the biocidal additive formulation. In another aspect of the invention, the ratio of ZnO to $Bi_2O_3$ is in a range of 1:2 to 1:3. The biocidal additive formulation is added to the glass as an additive package. The additive package is added in an amount of at least 1%, preferably 1% to 5%, wherein the percentage is based on a dry weight basis of the glass batch formulation to which it is added.

An example of a biocidal additive formulation in accordance with an aspect of the present invention comprises: 0.5% to 2.5% of a silver containing glass particle; 5% to 85% ZnO, preferably 25% to 85%; and 5% to 85% $Bi_2O_3$, preferably 10% to 35%, wherein percentages are by weight and are based on the dry weight of the biocidal additive formulation. In another aspect of the invention, the ratio of ZnO to $Bi_2O_3$ is an a ratio in a range of 2:1 to 3:1. The biocidal additive formulation is added to the glass as an additive package. The additive package is added in an amount of at least 2%, preferably 2% to 5%, wherein the percentage is based on a dry weight basis of the glass formulation to which it is added.

Without being bound by theory, it is believed that the silver containing glass particle preferentially distributes toward the surface of the skin glass during manufacture of the strengthened glass. The silver ions thereby are advantageously disposed toward the glass surface, rather than sequestered within the glass layers.

Likewise, it is theorized that the zinc- and bismuth-based compounds move through the skin layer during manufacture to become preferentially distributed "lower" in the skin layer, closer to the glass core. This phenomenon is believed to assist the silver-based compound in achieving a heterogeneous distribution closer to the skin layer surface.

The concentrations of the metal-based compounds may be raised until an unwanted effect is observe in either the manufacturing process or the finished product.

It should be understood that in certain situations the preferred type and quantity of biocidal additive may deviate from those presented herein. Those skilled in the art, however, should be able to take the present teachings and make the necessary adjustments without undue experimentation.

A second embodiment disclosed herein is a method for making a biocidal laminate glass. The method comprises adding an amount of the biocidal additive package to a glass batch formulation before and/or during the melting and refining process.

A third embodiment is a glass substrate possessing a durable biocidal property. The glass substrate comprises the biocidal additive package having the formulation of the present invention.

A fourth embodiment is an article constructed, in whole or in part, of a glass substrate possessing a durable biocidal property. The article comprises the biocidal additive package having the formulation of the present invention.

EXAMPLE

Manufacture

A biocidal additive formulation was comprised of a silver containing glass particle (IB14), ZnO, and $Bi_2O_3$. The IB14 was 1% by weight of the dry biocidal additive formulation/package. The ZnO and $Bi_2O_3$ was present in a ratio by weight of 2:1. This formulation was added as a package to a glass raw material at a concentration of 2% of the formulation on a dry weight basis of skin glass formulation. The conventional manufacturing process for this dishware otherwise was followed.

Physical Properties

Treated samples were evaluated for aesthetics and physical properties. The manufacturer's internal quality control tests were well within specifications for the treated samples.

Analyses were performed using X-Ray Fluorescence (XRF) to determine metal levels in the strengthened glass samples. The XRF readings showed very consistent levels of biocidal additive components by measurement of the silver, bismuth and zinc concentrations.

It also was observed, however, that the concentrations of the metal components slowly increased as the thermal mixing of the glass tank dispersed the materials over time. Time-stamped samples confirmed a correlation between manufacturing time point, amount of biocidal (metal) additives detected in the samples by XRF, and efficacy results.

Biocidal Activity Testing

Biocidal activity has been measured by quantifying the survival of bacterial cells which have been held in intimate contact with the test sample surface for 24 hours at 37 degrees C. with a relative humidity of 75%.

Biocidal activity was tested according to the ISO standardized test protocol 22196, entitled "Measurement of Antibacterial Activity on Plastics Surfaces" and commonly used in the assessment of antibacterial finishes on plastic, ceramic and glass surfaces.

No internationally standardized test protocol was approved and published for the testing of antibacterial/biocidal activity on glass surfaces as of the time of testing. Accordingly, a modified ISO 22196 protocol was used to determine biocidal activity.

The protocol was evaluated to ensure the viability of test organisms on an untreated glass slide control surface, making it possible to reliably compare the survival of these organisms with those applied to a biocidal treated test surface.

The biocidal effect is measured by comparing the survival of bacteria on a treated sample surface with that achieved on an untreated glass slide. This change is in accord with the new method for evaluating biocidal efficacy of glass and ceramic samples currently under consideration in ISO and ASTM committees.

For the purposes of this procedure, the test organism was *Escherichia coil* ATCC 8739. This microorganisms is maintained and commercially available from American Type Culture Collection (Manassas Va.).

Each trial was tested on multiple plates and also against a control plate. Three separate samples were taken from each plate and tested. The reported test result is the average of the three sample pieces.

Biocidal Performance

The addition of the formulation to the glass tank resulted in excellent efficacy results versus the untreated glass standard. The highest efficacy attained was a 2.6-log reduction. Results are shown in the Table 1:

TABLE 1

| PLATE | Log Reduction Status |
|---|---|
| Plate #1: Avg | 1.1 |
| Plate #2: Avg | 1.5 |
| Plate #3: Avg | 1.6 |
| Plate #4: Avg | 2.6 |

The 2.6-log reduction is a reduction of about 99.8% compared to the otherwise-identical untreated glass standard. This biocidal ability represents a significant differentiation between treated and untreated dishware.

The present strengthened glass advantageously may be employed in a variety of consumer, residential and commercial goods in which a durable biocidal property is desired. Representative articles or products include, without limitation, dishware, barware, glassware, device covers (e.g. automatic teller machines), automobile windows, partitions (e.g. display cases, commercial or residential windows), shelving, work surfaces (e.g. table and desk tops), touch screens (as found on, e.g., computers, tablets, cellphones, electronic book readers, automotive navigation and "infotainment" devices), and the like.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements.

What is claimed is:

1. A method for making a biocidal glass, the method comprising:
   adding a biocidal additive formulation comprised of a silver containing glass particle and at least two metal based compounds as an additive package to a glass batch formulation,
   wherein a metal in each of the metal based compounds is selected from the group consisting of a second silver, copper, zinc, mercury, tin, lead, bismuth, barium, cadmium, chromium, and a combination thereof, and
   wherein the additive package is added in an amount in a range of at least 1% based on a dry weight of the glass batch formulation.

2. The method according to claim 1, wherein the additive package is added in an amount in a range of 1% to 5% based on a dry weight of a glass batch formulation.

3. The method according to claim 1, wherein the metal of each of the metal based compounds is selected from the group consisting of a second silver, zinc, bismuth, and a combination thereof.

4. The method according to claim 1, wherein the at least two metal based compounds are ZnO and $Bi_2O_3$.

5. The method according to claim 1, wherein the silver containing glass particle is present in a range of 0.5% to 2.5%, based on the weight of the biocidal additive formulation.

6. The method according to claim 4, wherein ZnO is in a weight ratio to $Bi_2O_3$ in a range of 1:2 to 1:3.

7. The method according to claim 4, wherein ZnO is in a weight ratio to $Bi_2O_3$ in a range of 2:1 to 3:1.

8. A glass substrate possessing a durable biocidal property comprising a biocidal additive package having the formulation comprising:
    a silver containing glass particle, and
    a combination of at least two metal based compounds, wherein a metal in each of the metal based compounds is selected from the group consisting of a second silver, copper, zinc, mercury, tin, lead, bismuth, barium, cadmium, chromium, titanium, and a combination thereof, wherein the glass substrate is selected from the group consisting of sandwiched, tempered, strengthened, laminated, and a combination thereof.

9. An article constructed, in whole or in part, of a glass substrate possessing a durable biocidal property, the glass substrate comprising a biocidal additive package having the formulation comprising:
    a silver containing glass particle, and
    a combination of at least two metal based compounds, wherein a metal in each of the metal based compounds is selected from the group consisting of a second silver, copper, zinc, mercury, tin, lead, bismuth, barium, cadmium, chromium, titanium, and a combination thereof, wherein the glass substrate is selected from the group consisting of sandwiched, tempered, strengthened, laminated, and a combination thereof.

10. The article according to claim 9, wherein the article is dishware, barware, glassware, device cover, automobile window, partition, shelving, work surface, or a touch screen.

* * * * *